United States Patent [19]

Fisher

[11] Patent Number: 5,488,113
[45] Date of Patent: Jan. 30, 1996

[54] PROCESS FOR THE PREPARATION OF 1-HYDROXYINDOLE COMPOUNDS

[75] Inventor: Raymond Fisher, Hyde, United Kingdom

[73] Assignee: Eastman Chemical Company, Kingsport, Tenn.

[21] Appl. No.: 379,042

[22] Filed: Jan. 27, 1995

Related U.S. Application Data

[62] Division of Ser. No. 242,821, May 16, 1994, Pat. No. 5,434,271.

[51] Int. Cl.$^6$ .................................................. C07D 209/10
[52] U.S. Cl. ............................................................ 548/508
[58] Field of Search .................................................. 548/508

[56] References Cited

U.S. PATENT DOCUMENTS 3,296,277  1/1967  Petracek ............................... 548/505
5,118,695  6/1992  Schleigh et al. ...................... 514/339
5,183,894  2/1993  Schleigh et al. ...................... 546/273

OTHER PUBLICATIONS

Clark, R. et al., "Some Observations on the Formation of 1–Hydroxyindoles . . . " J. Het. Chem., vol. 22, pp. 121–125, 1985.

*Primary Examiner*—Jacqueline Haley
*Attorney, Agent, or Firm*—Karen A. Harding; Harry J. Gwinnell

[57] ABSTRACT

Disclosed is a process for the preparation of a novel class of 1-hydroxy-6-organosulphonylindoles comprising catalytically hydrogenating beta-dimethylamino-2-nitro-4-organosulphonylstyrenes.

3 Claims, No Drawings

PROCESS FOR THE PREPARATION OF 1-HYDROXYINDOLE COMPOUNDS

This is a divisional application of application Ser. No. 08/242,821 filed May 16, 1994, now U.S. Pat. No. 5,434,271.

This invention pertains to certain novel 1-hydroxyindole compounds and to a process for their preparation. More specifically, this invention pertains to 1-hydroxyindole compounds which are substituted at the 6-position with a sulphone group.

A number of 1-hydroxyindole compounds are known. U.S. Pat. Nos. 5,118,695 and 5,183,894 describe a broad class of fungicidally-active 1-hydroxyindoles which are substituted at the 2- and/or 3-positions. Japanese Published Patent Applications 57/085368 (1982) and 57/142968 (1982) disclose 4-substituted-1-hydroxyindoles which are stated to be useful intermediates in the preparation of pharmaceuticals and agrochemicals. A process for preparing a variety of 1-hydroxyindole compounds is described in Japanese Published Patent Application 3031257 (1991). U.S. Pat. No. 3,296,277 discloses 3-cyano-2-phenyl-1-hydroxyindoles wherein the phenyl group is substituted with an alkoxy or nitro group.

Kawasaki et al, Heterocycles, 32, 221–7 (1991) and the references cited therein disclose that due to its instability when isolated, 1-hydroxyindole normally is obtained as a solution. It is known that a nitro, cyano, and, to a lesser extent, a methoxycarbonyl group at the 4-position stabilizes the 1-hydroxyindole molecule significantly. Clark et al, J. Heterocycl. Chem., 22, 121 (1985) disclose that a cyano group at the 5- or 6-position also stabilizes the 1-hydroxyindole molecule but to a much lesser extent. With respect to 5- and 6-cyano-1-hydroxyindoles, Clark et al state: "The latter two crystalline compounds were stable when refrigerated (−20°) in the dark but decomposed at room temperature to highly colored by-products."

It has been discovered that 6-organosulphonyl-1-hydroxyindoles are stable compositions of matter. The compounds undergo little if any decomposition when stored at temperatures up to 20° C. Thus, one embodiment of the present invention comprises a class of novel 1-hydroxyindole compounds having the general formula:

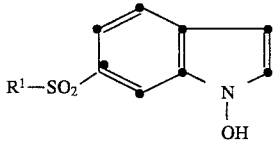

wherein $R^1$ represents an organic radical such as, for example, an unsubstituted or substituted alkyl, cycloalkyl or aryl group containing up to about 20 carbon atoms. Cyclopentyl, cyclohexyl, cycloheptyl, phenyl, and naphthyl are examples of the unsubstituted cycloalkyl and aryl which $R^1$ may represent. These cycloalkyl and aryl groups may be substituted with one or a plurality of groups which do not interfere with the preparation of the 1-hydroxyindole compounds according to the procedures described below. Alkyl of up to 4 carbon atoms, alkoxy of up to 4 carbon atoms and halogen are examples of such inert substituents. $R^1$ preferably represents alkyl of up to about 4 carbon atoms.

The novel 1-hydroxyindole compounds provided by the present invention are prepared by the hydrogenation of an enamine having the general formula:

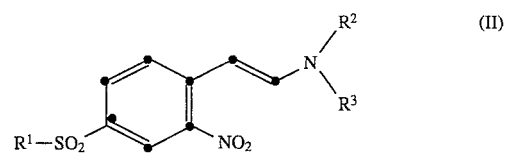

wherein $R^1$ is defined above and $R^2$ and $R^3$ each represent alkyl of up to 4 carbon atoms. The preparation of indoles by the hydrogenation of enamines similar to those having formula (II) is known. However, it also is known that hydrogenation of such similar enamines gives poor yields of the desired 1-hydroxyindole compound and/or results in the formation of by-products such as the analogous 1-unsubstituted-indole. See, for example, Clark et al, J. Heterocycl. Chem., 22, 121 (1985).

In contrast to the above-described known methods for synthesizing 1-hydroxy (and 1-unsubstituted) indoles, the novel compounds of formula (I) can be obtained in improved yields and purity. Therefore, a second embodiment of this invention provides a process for the preparation of a 1-hydroxyindole compound having the general formula:

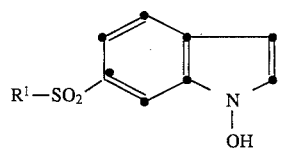

which comprises hydrogenating an enamine having the general formula:

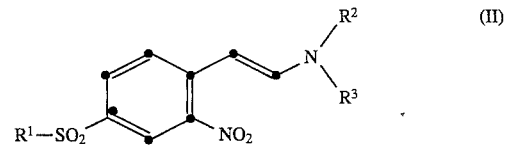

in the presence of tetrahydrofuran solvent and a catalytic amount of a palladium, platinum, rhodium or nickel hydrogenation catalyst under hydrogenation conditions of pressure and temperature.

The hydrogenation process may be carried out at a temperature of about 0° to 150° C. and a pressure of about 1 to 150 bars absolute. However, the preferred hydrogenation conditions comprise a temperature of about 50° to 70° C. and a pressure of about 2 to 30 bars absolute. The amount of tetrahydrofuran solvent employed can be varied substantially but normally will be an amount which will give a tetrahydrofuran:enamine (II) weight ratio in the range of about 2:1 to 20:1.

The metal hydrogenation catalysts may be unsupported or supported catalysts consisting of either the free metal or compounds of the metals such as halides, oxides or mixtures thereof. Examples of representative catalyst support materials include carbon, alumina, silica, silica/alumina, barium sulphate and like materials. The preferred hydrogenation catalysts comprise supported palladium catalysts wherein palladium metal comprises about 0.5 to 10 weight percent of the catalyst. Palladium on carbon catalysts are particularly preferred.

The enamines of formula (II) may be prepared according to known procedures by contacting a 2-nitro-4-organosulphonyl toluene compound with a dialkylformamide dialkyl acetal at elevated temperatures. The hydroxyindole compounds of formula (I) may be used as intermediates in the preparation of pharmaceuticals, agrochemicals and dyes. For example, the compounds of formula (I) may be coupled with diazotized amines to produce azo dyes according to well-known procedures. Alternatively, a formyl group may be added to the 5-position of the compounds of formula (I) by the Vilsmeir reaction and the resulting aldehydes may be condensed with an active methylene compound such as malononitrile to produce methine dyes.

The use of the process of this invention to prepare one of the novel 1-hydroxy-6-organosulphonylindole compounds is illustrated by the following example.

A 1-L pressure reactor was charged with 1-dimethylamino-2-(4-methylsulphonyl-2-nitrophenyl)ethene (54.0 g, 0.2 mol), 5.0% palladium on carbon hydrogenation catalyst (0.3 g) and tetrahydrofuran (500 mL). The reactor then was sealed, pressurized to approximately 30 bars absolute with hydrogen and heated with stirring to 50° C., at which point an exotherm caused the temperature to rise to approximately 85° C. The reaction mixture then was stirred at 60°–70° C. for 1 hour, after which time the reactor was cooled and vented. The reaction mixture was filtered to remove the catalyst and the filtrate was concentrated under reduced pressure to give a brown solid which was dissolved in ethyl acetate (500 mL) and washed with 1M aqueous hydrochloric acid (3×200 mL) and then water (2×200 mL). The organic layer was dried over magnesium sulfate and concentrated under reduced pressure to give a pale brown solid which was slurried in 53% weight:weight ethyl acetate in hexane (about 60 mL). The solid was collected by suction filtration and dried to give crude 1-hydroxy-6-methylsulphonylindole as a pale brown solid (33.1 g, 78% of theory). This crude product was recrystallized from acetonitrile to give a white crystalline product (17.8 g, 42% of theory). The filtrate from the recrystallization was concentrated in vacuo to a heavy slush which was cooled, filtered and washed with ice-cold acetonitrile to give a second crop of 1-hydroxy-6-methylsulphonylindole (10.7 g, 25% of theory) which was recrystallized twice from acetonitrile to give the product as a white, crystalline solid (3.8 g, 9% of theory). Thus, the total yield of 1-hydroxy-6-methylsulphonylindole was 21.6 g (51% of theory). Melting point 174°–176° C.; Rf (66% weight:weight ethyl acetate in hexane) 0.36. Calculated: C, 51.17; H, 4,29; N, 6.63. Found: C, 51.10; H, 4,16; N, 6.67.

The invention has been described in detail with particular reference to preferred embodiments thereof, but it will be understood that variations and modifications will be effected within the spirit and scope of the invention.

I claim:

1. Process for the preparation of a compound having the general formula

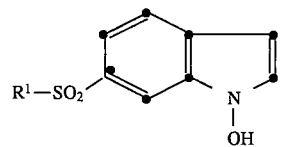

which comprises hydrogenating an enamine having the general formula

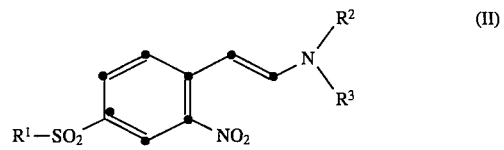

in the presence of tetrahydrofuran solvent and a catalytic amount of a palladium, platinum, rhodium or nickel hydrogenation catalyst under hydrogenation conditions of pressure and temperature, wherein $R^1$ is an organic radical and $R^2$ and $R^3$ each represent alkyl of up to 4 carbon atoms.

2. Process according to claim 1 wherein the pressure is in the range of about 2 to 30 bars absolute, the temperature is in the range of about 50° to 70° C., and $R^1$ is an unsubstituted or substituted alkyl, cycloalkyl or aryl radical containing up to about 20 carbon atoms.

3. Process for the preparation of a compound having the general formula

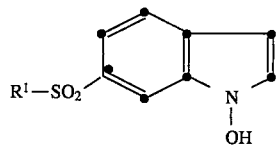

which comprises hydrogenating an enamine having the general formula

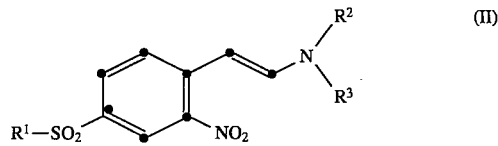

in the presence of tetrahydrofuran solvent and a catalytic amount of a supported palladium hydrogenation catalyst under a pressure of about 2 to 30 bars absolute and a temperature of about 50° to 70° C., wherein $R^1$ is alkyl of up to about 4 carbon atoms and $R^2$ and $R^3$ each represent methyl.

* * * * *